(12) United States Patent
Hodges

(10) Patent No.: US 7,431,820 B2
(45) Date of Patent: Oct. 7, 2008

(54) ELECTROCHEMICAL CELL

(75) Inventor: Alastair Hodges, Blackburn South (AU)

(73) Assignee: LifeScan, Inc., Milpitas, CA (US)

( * ) Notice: Subject to any disclaimer, the term of this patent is extended or adjusted under 35 U.S.C. 154(b) by 831 days.

(21) Appl. No.: 10/416,437

(22) PCT Filed: Oct. 1, 2002

(86) PCT No.: PCT/US02/31289

§ 371 (c)(1),
(2), (4) Date: Oct. 14, 2003

(87) PCT Pub. No.: WO03/032411

PCT Pub. Date: Apr. 17, 2003

(65) Prior Publication Data

US 2004/0065562 A1    Apr. 8, 2004

Related U.S. Application Data

(60) Provisional application No. 60/328,846, filed on Oct. 10, 2001.

(51) Int. Cl.
G01N 27/30 (2006.01)
G01N 27/327 (2006.01)

(52) U.S. Cl. .............. 205/777.5; 205/775; 204/403.02; 204/403.11

(58) Field of Classification Search ........... 204/403.01–403.15; 205/777.5, 778, 792
See application file for complete search history.

(56) References Cited

U.S. PATENT DOCUMENTS

| | | |
|---|---|---|
| 4,053,381 A | 10/1977 | Hamblen et al. |
| 4,076,596 A | 2/1978 | Connery et al. |
| 4,088,448 A | 5/1978 | Lilja et al. |
| 4,224,125 A | 9/1980 | Nakamura et al. |
| 4,233,029 A | 11/1980 | Columbus |
| 4,254,083 A | 3/1981 | Columbus |
| 4,254,546 A | 3/1981 | Ullery, Jr. |

(Continued)

FOREIGN PATENT DOCUMENTS

AU    3104293 A    7/1993

(Continued)

OTHER PUBLICATIONS

JPO English language computer translation of JP 05-002007 A. Date of publication of application: Aug. 1, 1993.*

(Continued)

*Primary Examiner*—Alex Noguerola
(74) *Attorney, Agent, or Firm*—Nutter McClennen & Fish LLP

(57) ABSTRACT

The present invention relates to electrochemical cells including a first working electrode 32, a first counter electrode 34, a second working electrode 36, and a second counter electrode 38, wherein the electrodes are spaced such that reaction products from the first counter electrode 34 arrive at the first working electrode 32, and reaction products from the first and second counter electrodes 34, 38 do not reach the second working electrode 36. Also provided is a method of using such electrochemical cells for determining the concentration of a reduced or oxidized form of a redox species with greater accuracy than can be obtained using an electrochemical cell having a single working and counter electrode.

26 Claims, 2 Drawing Sheets

U.S. PATENT DOCUMENTS

| | | | |
|---|---|---|---|
| 4,259,165 A | 3/1981 | Miyake et al. |
| 4,301,412 A | 11/1981 | Hill et al. |
| 4,301,414 A | 11/1981 | Hill et al. |
| 4,303,887 A | 12/1981 | Hill et al. |
| 4,307,188 A | 12/1981 | White |
| 4,319,969 A | 3/1982 | Oda et al. |
| 4,374,013 A | 2/1983 | Enfors et al. |
| 4,404,066 A | 9/1983 | Johnson |
| 4,431,004 A | 2/1984 | Bessman et al. |
| 4,431,507 A | 2/1984 | Nankai et al. |
| 4,508,613 A | 4/1985 | Busta et al. |
| 4,517,287 A | 5/1985 | Scheibe et al. |
| 4,517,291 A | 5/1985 | Seago |
| 4,533,440 A | 8/1985 | Kim |
| 4,545,382 A | 10/1985 | Higgins et al. |
| 4,552,840 A | 11/1985 | Riffer |
| 4,554,064 A | 11/1985 | McClintock et al. |
| 4,591,550 A | 5/1986 | Hafeman et al. |
| 4,629,563 A | 12/1986 | Wrasidlo |
| 4,654,197 A | 3/1987 | Lilja et al. |
| 4,664,119 A | 5/1987 | Bessman et al. |
| 4,711,245 A | 12/1987 | Higgins et al. |
| 4,774,039 A | 9/1988 | Wrasidlo |
| 4,782,265 A | 11/1988 | Schaper et al. |
| 4,790,925 A | 12/1988 | Miller et al. |
| 4,897,173 A | 1/1990 | Nankai et al. |
| 4,900,424 A | 2/1990 | Birth et al. |
| 4,911,794 A | 3/1990 | Parce et al. |
| 4,919,770 A | 4/1990 | Preidel et al. |
| 4,963,815 A | 10/1990 | Hafeman |
| 4,988,429 A | 1/1991 | Matthiessen et al. |
| 4,989,452 A | 2/1991 | Toon et al. |
| 5,059,908 A | 10/1991 | Mina |
| 5,064,516 A | 11/1991 | Rupich |
| 5,089,112 A | 2/1992 | Skotheim et al. |
| 5,089,320 A | 2/1992 | Straus et al. |
| 5,095,407 A | 3/1992 | Kanezawa et al. |
| 5,108,564 A | 4/1992 | Szuminsky et al. |
| 5,120,420 A | 6/1992 | Ohtani et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,151,166 A | 9/1992 | Harral et al. |
| 5,156,972 A | 10/1992 | Issachar et al. |
| 5,171,689 A | 12/1992 | Kawaguri et al. |
| 5,192,415 A | 3/1993 | Yoshioka et al. |
| 5,229,282 A | 7/1993 | Yoshioka et al. |
| 5,243,516 A | 9/1993 | White |
| 5,243,526 A | 9/1993 | Ito et al. |
| 5,269,903 A | 12/1993 | Ikariyama et al. |
| 5,272,087 A | 12/1993 | El Murr et al. |
| 5,282,950 A | 2/1994 | Dietze et al. |
| 5,312,590 A | 5/1994 | Gunasingham et al. |
| 5,314,605 A | 5/1994 | Matthiessen et al. |
| 5,320,732 A | 6/1994 | Nankai et al. |
| 5,366,609 A | 11/1994 | White et al. |
| 5,382,346 A | 1/1995 | Uenoyama et al. |
| 5,384,028 A | 1/1995 | Ito |
| 5,385,846 A | 1/1995 | Kuhn et al. |
| 5,388,163 A | 2/1995 | Elko et al. |
| 5,393,399 A | 2/1995 | Van den Berg et al. |
| 5,395,504 A | 3/1995 | Saurer et al. |
| 5,399,256 A | 3/1995 | Bohs et al. |
| 5,413,690 A | 5/1995 | Kost et al. |
| 5,437,999 A | 8/1995 | Diebold et al. |
| 5,443,710 A | 8/1995 | Broderick |
| 5,496,453 A | 3/1996 | Uenoyama et al. |
| 5,508,171 A | 4/1996 | Walling et al. |
| 5,509,410 A | 4/1996 | Hill et al. |
| 5,512,159 A | 4/1996 | Yoshioka et al. |
| 5,517,313 A | 5/1996 | Colvin, Jr. |
| 5,518,590 A | 5/1996 | Fang |
| 5,520,787 A | 5/1996 | Hanagan et al. |
| 5,527,446 A | 6/1996 | Kosek et al. |
| 5,567,302 A | 10/1996 | Song et al. |
| 5,575,895 A | 11/1996 | Ikeda et al. |
| 5,607,565 A | 3/1997 | Azarnia et al. |
| 5,611,908 A | 3/1997 | Matthiessen et al. |
| 5,620,579 A | 4/1997 | Genshaw et al. |
| 5,628,890 A | 5/1997 | Carter et al. |
| 5,645,709 A | 7/1997 | Birch et al. |
| 5,651,869 A | 7/1997 | Yoshioka et al. |
| 5,682,884 A | 11/1997 | Hill et al. |
| 5,695,947 A | 12/1997 | Guo et al. |
| 5,726,565 A | 3/1998 | Uchiyama et al. |
| 5,727,548 A | 3/1998 | Hill et al. |
| 5,762,770 A | 6/1998 | Pritchard et al. |
| 5,849,174 A | 12/1998 | Sanghera et al. |
| 5,863,400 A | 1/1999 | Drummond et al. |
| 5,909,114 A | 6/1999 | Uchiyama et al. |
| 5,942,102 A | 8/1999 | Beck et al. |
| 5,997,817 A | 12/1999 | Crismore et al. |
| 6,071,391 A | 6/2000 | Gotoh et al. |
| 6,117,289 A | 9/2000 | Yamamoto et al. |
| 6,153,069 A | 11/2000 | Pottgen et al. |
| 6,174,420 B1 | 1/2001 | Hodges et al. |
| 6,179,979 B1 | 1/2001 | Hodges et al. |
| 6,193,873 B1 | 2/2001 | Ohara et al. |
| 6,214,205 B1 | 4/2001 | Willner et al. |
| 6,218,134 B1 | 4/2001 | Yamauchi et al. |
| 6,251,260 B1 | 6/2001 | Heller et al. |
| 6,270,637 B1 | 8/2001 | Crismore et al. |
| 6,284,125 B1 | 9/2001 | Beck et al. |
| 6,325,973 B1 | 12/2001 | Leland et al. |
| 6,863,801 B2 | 12/2001 | Hodges et al. |
| 6,413,395 B1 | 7/2002 | Bhullar et al. |
| 6,413,410 B1 | 7/2002 | Hodges et al. |
| 6,461,496 B1 | 10/2002 | Feldman et al. |
| 6,503,381 B1 | 1/2003 | Gotoh et al. |
| 6,521,110 B1 | 2/2003 | Hodges et al. |
| 6,544,212 B2 | 4/2003 | Galley et al. |
| 6,780,756 B1 | 8/2004 | Farber et al. |
| 2002/0012943 A1 | 1/2002 | Fowlkes et al. |

FOREIGN PATENT DOCUMENTS

| | | |
|---|---|---|
| AU | 5487394 | 8/1994 |
| DE | 3103464 | 8/1982 |
| DE | 29709141 | 8/1997 |
| EP | 0125137 | 11/1984 |
| EP | 0127958 | 12/1984 |
| EP | 0170375 B1 | 2/1986 |
| EP | 0251915 | 1/1988 |
| EP | 0255291 A1 | 2/1988 |
| EP | 0266204 | 5/1988 |
| EP | 0278647 | 8/1988 |
| EP | 0290770 | 11/1988 |
| EP | 0299779 | 1/1989 |
| EP | 0351516 | 1/1990 |
| EP | 0351891 | 1/1990 |
| EP | 0351892 A2 | 1/1990 |
| EP | 0359831 | 3/1990 |
| EP | 0367432 | 5/1990 |
| EP | 0400918 | 12/1990 |
| EP | 0406304 | 1/1991 |
| EP | 0418404 | 3/1991 |
| EP | 0422708 | 4/1991 |
| EP | 0451981 A2 | 10/1991 |
| EP | 0560336 A1 | 9/1993 |
| EP | 0585933 | 3/1994 |
| EP | 0593096 | 4/1994 |
| EP | 0603954 | 6/1994 |
| EP | 0609760 A1 | 8/1994 |

| | | |
|---|---|---|
| EP | 0735303 | 10/1996 |
| EP | 0741186 | 11/1996 |
| EP | 0764469 | 3/1997 |
| EP | 0964059 | 12/1999 |
| GB | 2020424 | 11/1979 |
| GB | 2154735 | 9/1985 |
| GB | 2194112 | 2/1988 |
| GB | 2201248 | 8/1988 |
| GB | 2215846 | 9/1989 |
| GB | 2235050 | 2/1991 |
| JP | 54006595 | 1/1979 |
| JP | 59003345 | 1/1984 |
| JP | 60017344 | 1/1985 |
| JP | 60244853 | 12/1985 |
| JP | 60250246 | 12/1985 |
| JP | 61002060 | 1/1986 |
| JP | 62228274 | 10/1987 |
| JP | 63139246 | 6/1988 |
| JP | 1253648 | 10/1989 |
| JP | 3167464 | 7/1991 |
| JP | 4062463 | 2/1992 |
| JP | 4066112 | 3/1992 |
| JP | 4343065 | 11/1992 |
| JP | 5002007 | 1/1993 |
| JP | 5080018 | 3/1993 |
| JP | 5312761 | 11/1993 |
| JP | 6222874 | 8/1994 |
| JP | 6310746 | 11/1994 |
| JP | 8062179 | 3/1996 |
| JP | 8304340 | 11/1996 |
| JP | 9222408 | 8/1997 |
| JP | 9236570 | 9/1997 |
| JP | 9243588 | 9/1997 |
| JP | 2007225619 | 9/2007 |
| RU | 1806187 A3 | 3/1993 |
| RU | 2046361 | 10/1995 |
| SU | 1351627 | 11/1987 |
| WO | WO-8908713 | 9/1989 |
| WO | 9005910 | 5/1990 |
| WO | 9109139 | 6/1991 |
| WO | WO-9215701 | 9/1992 |
| WO | WO-9402842 | 2/1994 |
| WO | WO-9429731 | 12/1994 |
| WO | WO-9516198 | 6/1995 |
| WO | WO-9521934 | 8/1995 |
| WO | WO-9528634 | 10/1995 |
| WO | WO-97/00441 A1 * | 1/1997 |
| WO | WO-9718464 | 5/1997 |
| WO | WO-9718465 | 5/1997 |
| WO | WO-9811426 | 3/1998 |
| WO | WO-9843073 | 10/1998 |
| WO | WO-9843074 | 10/1998 |
| WO | WO-9946585 | 9/1999 |
| WO | WO 0020626 A | 4/2000 |
| WO | WO-0208763 | 1/2002 |

OTHER PUBLICATIONS

International Search Report, dated Jul. 18, 2003, issued by the European Patent Office, PCT/US02/31289.
Anderson, et al., Diagnostic Criteria for the Study of Chemical and Physical Processes by Twin-Electrode Thin-Layer Electrochemistry, J. Electroanalytical Chemistry; vol. 12, 1966, pp. 477-494.
Anderson, et al., Thin-Layer Electrochemistry: Steady-State Methods of Studying Rate Processes,J. Electroanalytical Chemistry; vol. 10, 1965, pp. 295-305.
Cassidy, et al.; Novel Electrochemical Device for the Detection of Cholesterol or Glucose, Analyst, vol. 118; Apr. 1993; pp. 415-418.
Chidsey, et al., Micrometer-Spaced Platinum Interdigitated Array Electrode: Fabrication, Theory, and Initial Use, Analytical Chemistry, vol. 58, No. 3, Mar. 1986, pp. 801-807.
Christensen, et al. Chronopotentiometry in Thin Layers of Solution, Analytical Chemistry, vol. 35, No. 2, 1963, pp. 205-209.
Daruhazi, et al., "Cyclic Voltammetry for Reversible Redox-Electrode Reaction in Thin Layer Cells with Closely Separated Working and Auxiliary Electrodes of the Same Size", in J. Electroanal. Chem. 264; 77-89 (1989).
Denuault, et al., Direct Determination of Diffusion-Coefficients by Chronoamperometry at Microdisk Electrodes, Journal of Electroanalytical Chemistry, vol. 308, No. 1-2, 1991, pp. 27-38.
Enthone—Imaging Technologies Update Jun. 2001/No. 3.
European Search Report for App. No. 03 00 7604 dated May 19, 2003.
European Search Report for App. No. 96 93 7919.
European Search Report for App. No. 99 20 2305.
Hall, E., Biosensors, Chapter 5: "Amperometric Assay Techniques", 1990.
Hubbard, et al., New Electrodes for Chronopotentiometry in Thin Layers of Solution, Analytical Chemistry, vol. 36, No. 4, Apr. 1964, pp. 723-728.
Hubbard, et al., The Theory and Practice of Electrochemicsty with Thin Layer Cells, in Electroanalytical Chemistry, (Bard, Ed.), Marcel Deletier, New York, 1970, vol. 4 (pp. 129-214).
Hubbard, Study of the Kinetics of Electrochemical Reactions by Thin—Layer Voltammetry, J. Electroanalytical Chemistry, vol. 22, 1969, pp. 165-174.
Jung, et al., Simultaneous Determination of Diffusion Coefficient and Concentration by Chronoamperometry at a Microdisk Electrode, Bull Korean Chem. Soc.; 1004, V. 15, No. 3, pp. 209-213 1994.
McDuffie, et al., Twin electrode thin-Layer Electrochemistry, Analytical Chemistry, vol. 38, No. 7, Jun. 1966; pp. 883-890.
Morris, et al., Electrochemistry at Pt Band Electrodes of Width Appraching Molecular Dimensions, Breakdown of Transport Equaltions at Very Small Electrodes, J. of Physical Chemistry, vol. 91, No. 13, 1987, pp. 3559-3564.
Nicholson, et al., Theory of Stationary Electrode Polarography, Analytical Chemistry; vol. 36, No. 4, Apr. 1964, pp. 706-723.
Niwa, et al., Electrochemical Behavior of Reversiblel Redox Species at Interdigitated Array Electrodes with Different Geometries: Consideration of Redox Cycling and Collection Efficiency, Analytical Chemistry; Mar. 1990, vol. 62, No. 5, pp. 447-452.
Niwa, et al., Highly Selective electrochemical Detection of Dopamine Using Interdigitated Array of Electrodes Modified with Nafion/Polyester Ionomer Layered Film, Electroanalysis, vol. 6, No. 3, Mar. 1994, pp. 237-243, XP000943528.
Oglesby, et al., Thin Layer Electrochemical Studies Using Controlled Potential or Controlled Current, Analytical Chemistry, vol. 37, No. 11, Oct. 1965, pp. 1312-1316.
Paeschke, et al., Dynamic Redox Recycling of Cytochrome C, Journal of Electroanalytical Chemistry; vol. 393, No. 1/02, 1995, pp. 131-135.
Paeschke, et al., Properties of Interdigital Electrode Arrays With Different Geometries, Analytical Chimica Acta; vol. 305, No. 1/03, 1995, pp. 126-136.
Pickup, et al., Redox Conduction in Single and Bilayer Films of Redox Polymer, J. Amer. Chem. Soc.; vol. 106; No. 7; 1984.
Reilley, Charles, Electrochemistry Using Thin-Layer Cells, Review of Pure and Appl. Chem, vol. 18, 1968, pp. 137-151.
Salbeck, J., Spectrochemical Thin-Layer Cell for Nonaqueous Solvent Systems, Anal. Chem., 1993, vol. 65, pp. 2165-2173.
Seddon, et al., Preparation and Ameprometric Response of Carbon and Platinum Dual Cylinder Microelectrodes, Electrochimica Acta, vol. 40, No. 4, Mar. 1, 1995, pp. 455-465.
Specification sheet for Adhesives Research, Inc. ARClad® 8314 (May 2, 1997) (1 pg.)
Specification sheet for Adhesives Research, Inc., ARCare® 7148, double-sided adhesive coated polyester film (Mar. 30, 1995) (2 pages).
Trojanek, et al., Data processing in reaction rate measurements, Collect. Chzech. Chem commun., 38(9):2572-2580, 1973.
Uchiyama, et al., Measurement Of Homogeneous Reaction Rate By Concentration-Step, Controlled Potential Electrolysis, J. Electroanal. Chem Interfacial Electrochem., 91(3):301-308, 1978.

Yaoita, et al., Pulse Chronoamperometric Technique of Enzyme Embodied Electrode Applied to Glucose Measurement in Whole Serum. Extended Abstracts, US, Electrochemical Society. Princeton, NJ; vol. 93/1, 1993, p. 2801.

Abstract for JP1294453, publ. date Nov. 28, 1989, Youken KK (applicant).

Vldal, J.C. et al., "A Chronoamperometric Sensor for Hydrogen Peroxide Based on Electron Transfer Between Immobilized Horseradish Peroxidase on a Glassy Carbon Electrode and a Diffusing Ferrocene Mediator", Sensors and Actuators B:Chemical, vol. 21, Issue 2, Aug. 1994, pp. 135-141.

* cited by examiner

ELECTROCHEMICAL CELL

This application is a 371 of PCT/US02/31289, filed on Oct. 01, 2002, which claims the benefit of U.S. provisional application No. 60/328,846, filed on Oct. 10, 2001.

FIELD OF THE INVENTION

The present invention relates to electrochemical cells including, a first working electrode, a first counter electrode, a second working electrode and a second counter electrode, wherein the electrodes are spaced such that reaction products from the first counter electrode arrive at the first working electrode, and reaction products from the first and second counter electrodes do not reach the second working electrode. Also provided is a method of using such electrochemical cells for determining the concentration of a reduced or oxidized form of a redox species with greater accuracy than can be obtained using an electrochemical cell having a single working and counter electrode.

BACKGROUND OF THE INVENTION

In amperometric electrochemistry the current flowing at the electrode can be used as a measure of the concentration of electroactive species being reacted electrochemically at the working electrode. In coulometry the current flowing at the electrode can be integrated over time to give a total amount of charge passed which yields a measure of the amount of electroactive material reacted at the working electrode. The current flowing (or charge passed at any time) at the electrode depends upon the rate of transfer of the electroactive species to the working electrode. When a significant concentration of electroactive species is situated close to the electrode and an electrical potential is applied to the electrode sufficient to electrochemically react the electroactive species at the electrode/solution interface, initially a higher current flows which diminishes with time. For an isolated and substantially planar electrode, where the. potential applied to the electrode is sufficient to react the electroactive species effectively instantaneously upon arriving at the electrode and the transfer of electroactive species to the electrode is controlled by diffusion, the current follows a curve known in the art as the Cottrell Equation. According to this equation the current varies inversely with the square root of time. This yields a current which decays with time as the electroactive species that reacts at the electrode becomes depleted close to the electrode and so electroactive species has to travel from further and further away to reach the electrode as time progresses.

If, in addition to the electrochemical reaction of the electroactive species at the electrode, the electroactive species is generated close to the working electrode by a chemical reaction, the form of the current flowing at the electrode becomes complex. The electrode reaction tends to decrease the concentration of electroactive species close to the working electrode whereas the chemical reaction tends to increase the concentration of the electroactive species in this region. The time dependent behavior of these two processes therefore mix and it can be difficult to measure the chemical reaction kinetics from the current flowing (or charge passed) at the electrode.

For this reason, in the published literature, the rates of chemical reactions are not generally measured electrochemically except in specialized applications using specialized equipment. An example of such equipment is known in the art as a rotating ring/disc electrode. This apparatus is only applicable to relatively fast reaction kinetics and requires that the electrode be rotated at a known controlled rate with well-characterized liquid hydrodynamics.

SUMMARY OF THE INVENTION

An electrochemical cell and method of using such an electrochemical cell for determining the concentration of a reduced or oxidized form of a redox species with greater accuracy than can be obtained using an electrochemical cell having a single working and counter electrode is desirable. The preferred embodiments provide such electrochemical cells and methods.

In a first embodiment, a method for determining the concentration of a reduced or oxidized form of a redox species is provided, the method including the steps of: providing an electrochemical cell including a first working electrode, a first counter electrode, a second working electrode and a second counter electrode; selecting the spacing between the first working electrode and the first counter electrode so that reaction products from the first counter electrode arrive at the first working electrode; selecting the spacing between the first working electrode and the second counter electrode so that a significant amount of reaction products from the second counter electrode do not arrive at the first working electrode; selecting the spacing between the second working electrode and the second counter electrode so that a significant amount of reaction products from the second counter electrode do not arrive at the second working electrode; applying an electric potential difference between the first working electrode and the first counter electrode; applying an electric potential difference between the second working electrode and second counter electrode; selecting the potential of the first working electrode such that the rate of electro-oxidation of the reduced form or electro-reduction of the oxidized form of the species is diffusion controlled; selecting the potential of the second working electrode such that the rate of electro-oxidation of the reduced form or electro-reduction of the oxidized form of the species is diffusion controlled; subtracting a current flowing between the second working electrode and the second counter electrode from a current flowing between the first working electrode and the first counter electrode, whereby a corrected current is obtained; and obtaining from the corrected current a value indicative of the concentration of the reduced form or the oxidized form of the species.

In one aspect of the first embodiment, the surface area of the first working electrode and a surface area of the second working electrode are substantially the same.

In another aspect of the first embodiment, the surface area of the first working electrode and a surface area of the second working electrode are different, and the step of subtracting a current includes: determining a current flowing between the first working electrode and the first counter electrode; determining a current flowing between the second working electrode and the second counter electrode; normalizing the current flowing between the first working electrode and the first counter electrode and the current flowing between the second working electrode and the second counter electrode to a same electrode surface area to yield a normalized current flowing between the first working electrode and the first counter electrode and a normalized current flowing between the second working electrode and the second counter electrode; and subtracting the normalized current flowing between the second working electrode and the second counter electrode from the normalized current flowing between the first working electrode and the first counter electrode, whereby a corrected current is obtained.

In a further aspect of the first embodiment, the first working electrode and the first counter electrode are separated by less than about 500 μm, or by less than about 200 μm. The second working electrode and the second counter electrode or the first working electrode and the second counter electrode are separated by more than about 500 μm, or by more than about 1 mm.

In yet another aspect of the first embodiment, the redox species may be a mediator. When the redox species is a mediator, the concentration of the reduced or oxidized form of the mediator is indicative of the concentration of an analyte and wherein a measure of the diffusion coefficient of the reduced or oxidized form of the mediator is determined as a precursor to the determination of the concentration of the analyte.

In a further aspect of the first embodiment, the electrochemical cell additionally includes a separate reference electrode.

In yet another aspect of the first embodiment, the analyte may be glucose.

In a second embodiment, an electrochemical cell is provided including a first working electrode, a first counter electrode, a second working electrode and a second counter electrode, the first working electrode being spaced from the first counter electrode by less than about 500 μm, the first working electrode being spaced from the second counter electrode by more than about 500 μm, and the second working electrode being spaced from the second counter electrode by more than about 500 μm.

In one aspect of the second embodiment, the first working electrode and the first counter electrode and/or the second working electrode and the second counter electrode are facing one another or are in a side-by-side configuration.

In another aspect of the second embodiment, the first working electrode and the second working electrode are of substantially corresponding area.

In a further aspect of the second embodiment, the electrochemical cell further includes a separate reference electrode.

In yet another aspect of the second embodiment, the electrochemical cell may be a hollow electrochemical cell. The electrochemical cell can have an effective cell volume of less than 1.5 microliters.

In a third embodiment, an apparatus for determining the concentration of a redox species in an electrochemical cell is provided including: an electrochemical cell having a first working electrode, a first counter electrode, a second working electrode and a second counter electrode, characterized in that the first working electrode is spaced from the first counter electrode by less than 500 μm, the first working electrode is spaced from the second counter electrode by more than 500 μm, and the second working electrode is spaced from the second counter electrode by more than 500 μm; means for applying an electric potential difference between the first working electrode and the first counter electrode; and means for applying an electric potential difference between the second working electrode and the second counter electrode.

In one aspect of the third embodiment, the apparatus may be a glucose meter.

In a fourth embodiment, an electrochemical cell is provided including a first working electrode, a first counter electrode, and a second working electrode, the first working electrode being spaced from the first counter electrode by less than about 500 μm, and the second working electrode being spaced from the first counter electrode by more than about 500 μm.

In a fifth embodiment, a method for determining the concentration of a reduced or oxidized form of a redox species is provided, the method including the steps of: providing an electrochemical cell including a first working electrode, a counter electrode, and a second working electrode; selecting the spacing between the first working electrode and the counter electrode so that reaction products from the counter electrode arrive at the first working electrode; providing a redox species, wherein at least a useful fraction of the redox species initially present in the solution above the second working electrode has been reduced or oxidized at the second working electrode; applying an electric potential difference between the first working electrode and the counter electrode; selecting the potential of the first working electrode such that the rate of electro-oxidation of the reduced form or electro-reduction of the oxidized form of the species is diffusion controlled; determining a current flowing between the first working electrode and the counter electrode; and obtaining from the current a value indicative of the concentration of the reduced form or the oxidized form of the species.

In one aspect of the fifth embodiment, a surface area of the first working electrode and a surface area of the second working electrode are substantially the same.

In another aspect of the fifth embodiment, a surface area of the first working electrode and a surface area of the second working electrode are substantially different.

In a sixth embodiment, a method for determining the concentration of a reduced or oxidized form of a redox species is provided, the method including the steps of: providing an electrochemical cell including a first working electrode, a second working electrode, and a counter electrode; selecting the spacing between the first working electrode and the counter electrode so that reaction products from the counter electrode arrive at the first working electrode; selecting the spacing between the second working electrode and the counter electrode so that a significant amount of reaction products from the counter electrode do not arrive at the second working electrode; applying an electric potential difference between the second working electrode and the counter electrode whereby the second working electrode is substantially charged and whereby surface group reactions are substantially completed; interrupting the circuit between the second working electrode and the counter electrode before a significant amount of the species is reacted at the second working electrode; applying an electric potential difference between the first working electrode and the counter electrode; selecting the potential of the first working electrode such that the rate of electro-oxidation of the reduced form or electro-reduction of the oxidized form of the species is diffusion controlled; determining a current flowing between the first working electrode and the counter electrode; and obtaining from the current a value indicative of the concentration of the reduced form or the oxidized form of the species.

In a seventh embodiment, a method for determining the concentration of a reduced or oxidized form of a redox species is provided, the method including the steps of: providing an electrochemical cell including a first working electrode, a second working electrode, and a counter electrode; selecting the spacing between the first working electrode and the counter electrode so that reaction products from the counter electrode arrive at the first working electrode; selecting the spacing between the second working electrode and the counter electrode so that a significant amount of reaction products from the counter electrode do not arrive at the second working electrode; applying an electric potential difference between the second working electrode and the counter electrode and between the first working electrode and the counter electrode, whereby the second working electrode and first working electrode are substantially charged and whereby surface group reactions are substantially completed; interrupting the circuit between the second working electrode and the counter electrode before a significant amount of the species is reacted at the second working electrode; applying an electric potential difference between the first working electrode and the counter electrode; selecting the potential of the first working electrode such that the rate of electro-oxidation of the reduced form or electro-reduction of the oxidized form of the species is diffusion controlled; determining a current flowing between the first working electrode and the counter electrode; and obtaining from the current a value indicative of the concentration of the reduced form or the oxidized form of the species.

DETAILED DESCRIPTION OF THE PREFERRED EMBODIMENT

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

It may be desirable when using electrochemical cells as amperometric sensors for the detection and quantification of analytes to be able to detect very low concentrations of the analyte. One of the limitations of the prior art in detecting low concentrations of an analyte can be the presence of extraneous currents masking the current of interest. Some of these unwanted currents arise from the capacitive charging current of the electrode and electrical noise picked up from the environment. The preferred embodiments are directed towards a method for minimizing the contribution of these currents to the overall signal, allowing for improved detection of the analyte.

As is known in the prior art, electrodes in a two or three electrode electrochemical cell can be positioned such that the working electrode is isolated from the counter electrode reactions and reaction products or such that products of the counter electrode reaction diffuse to the working electrode where they react. The former type of electrochemical cell is well known in the prior art. The latter type of electrochemical cell is discussed in U.S. Pat. Nos. 6,179,979 and 5,942,102.

These two electrode configurations vary in that in the isolated case, the counter electrode is positioned far enough away from the working electrode such that during the time the cell is being used, products of electrochemical reactions at the counter electrode do not reach the working electrode. In practice, this is typically achieved by a separation of the working electrode from the counter electrode by at least a millimeter.

In the non-isolated configuration, the working electrode and the counter electrode are placed close enough together such that products of the electrochemical reactions at the counter electrode can diffuse to the working electrode during the time the cell is being used. These reaction products can then react at the working electrode, giving a higher current than may be present in the isolated electrode case. In the non-isolated configuration, the working electrode reactions can be described as coupled to the counter electrode reactions.

Electrode Configurations

Figure 1:
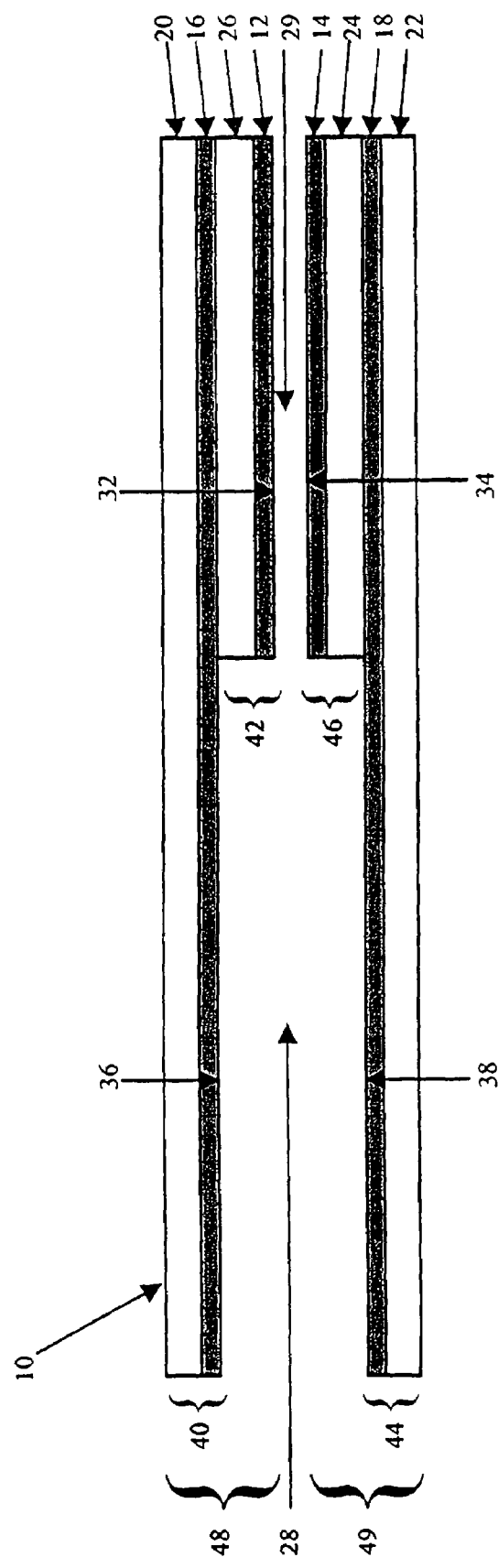
FIG. 1 shows a cross-section schematic of an electrochemical cell 10 of a preferred embodiment with electrode surfaces in a parallel and opposed configuration.
Figure 2:
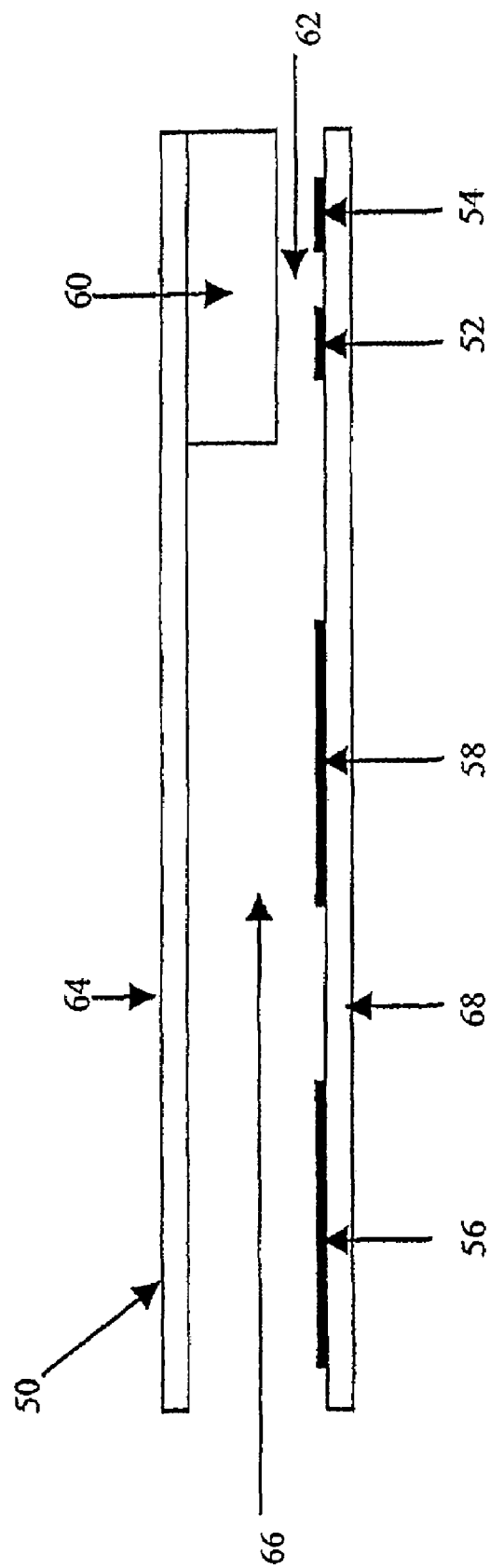
FIG. 2 shows a cross-section schematic of an electrochemical cell 50 of a preferred embodiment with electrodes in a side-by-side configuration.

In a preferred embodiment, isolated working electrodes and working electrodes coupled to a counter electrode are combined in an electrochemical cell to yield improved detection of low concentration species. FIGS. 1 and 2 illustrate different electrode configurations in electrochemical cells of preferred embodiments.

FIG. 1 shows a cross-section schematic of an electrochemical cell 10 of a preferred embodiment. The exposed portions of electrically conductive layers 12, 14, 16, 18 function as electrodes 32, 34, 36, 38 in the cell 10. The electrically conductive layers 12, 14, 16, 18 are in contact with layers 20, 22, 24, 26 of electrically resistive material. One or more spacer layers (not illustrated) maintain the separation of the electrodes 32, 34 to less than 500 µm. Either electrode 32 or electrode 34 or electrode 36 or electrode 38 can be working electrodes, provided that electrode 32 and 34 form one working and counter electrode pair and that electrode 36 and electrode 38 form another working and counter electrode pair. The thicknesses of layer 24 and layer 26 are such that separation between the closest edges of electrode 32 and electrode 36, and between the closest edges of electrode 34 and electrode 38 are all typically greater than 500 µm, preferably greater than 1 mm. In another embodiment, the layer of electrically resistive material 20 or 22 and the conductive layer 16 or 18 it supports may be substituted by a single layer of a suitable electrically conductive material (not illustrated), such as, for example, aluminum foil or a conducting polymer. For ease of fabrication, in certain embodiments it may be desirable to completely cover one surface of one or more of the layers of electrically resistive material 20, 22, 24, 26 with an electrically conductive layer 12, 14, 16, 18. Alternatively, in other embodiments it may be desirable to only partially cover the electrically resistive material 20, 22, 24, 26 with an electrically conductive layer 12, 14, 16, 18, for example, to save on materials costs if the electrode material comprises a noble metal. For example, in a cell 10 as illustrated in FIG. 1, the conductive layer 12 may only cover the portion of the insulating layer 26 adjacent to the sample reservoir 28. The portion of the insulating layer 20 adjacent to layer 26 is not covered. Other configurations of the electrically conducting layer 12, 14, 16, 18 and its adjacent layer of electrically resistive material 20, 22, 24, 26 will be apparent to one skilled in the art.

Another electrode configuration in an electrochemical cell 50 of a preferred embodiment is shown in FIG. 2. In this configuration, the electrodes 52, 54, 56, 58 are all on the same plane. A spacer layer 60 positioned over electrode 52 and electrode 54 is depicted in FIG. 2. When the electrochemical cell 50 is used in conjunction with a current subtraction method as described below, it may be preferred to omit the spacer layer 60. When the spacer layer 60 is omitted, the planar diffusion to electrode 54 more closely matches the planar diffusion to electrode 58, resulting in a more accurate current subtraction.

When the electrochemical cell 50 is used in conjunction with a current amplification method as described below, then it is preferred to maintain the spacer layer above electrode 52 and electrode 54 so as to provide a smaller volume of space 62 and a corresponding higher amplification factor than if the spacer layer 60 were not there. One or more spacer layers (not illustrated) maintains the separation of the electrodes 52, 54, 56, 58 from layer 64, thereby providing a sample reservoir 66 in the electrochemical cell 50. The distance between the closest edges of electrode 52 and electrode 54 is less than 500 μm, preferably less than about 450, 400, 350, 300, or 250 μm, more preferably less than about 200, 150, or 100 μm, and most preferably less than about 90, 80, 70, 60, 50, 40, 30, 25, 20, 15, 10, 5 or 1 μm. The separation between the closest edges of electrode 52 and electrode 58, and between the closest edges of electrode 54 and electrode 58 are typically greater than about 500 μm, preferably greater than about 550, 600, 650, 700, 750, 800, 850, 900, or 950 μm, and most preferably greater than 1, 2, 3, 4, 5, 6, 7, 8, 9, 10, 25, or 50 mm. However, any suitable spacing, including spacings less than about 500 μm, may be suitable so long as a significant amount of the products of reaction at the first electrode do not reach the second electrode. In this context a significant amount of reaction products is an amount sufficient to give rise to an extra amount of current at the second electrode that is large enough that it effects the practical utility of the methods of use of the cells to achieve the desired outcomes. In certain embodiments, it may be preferred to omit any spacer layers and layer 64, thereby providing an electrochemical cell including the electrodes 52, 54, 56, 58 on a single layer of electrically resistive material 68. This embodiment may be preferred when sample sizes are sufficient such that the layer 68 and electrodes 52, 54, 56, 58 may be immersed in the sample, or a sufficient layer of sample may be applied to electrodes 52, 54, 56, 58.

As will be apparent to one skilled in the art, different electrode configurations maintaining the appropriate spacing between electrodes 52, 54, 56, 58 may be preferred in various embodiments. For example, the electrochemical cell 50 illustrated in FIG. 2 may be modified by placing one or both of electrodes 56 and 58 on layer 64 instead of layer 68. Alternatively, one or both of electrodes 52 and 54 may be placed on layer 64 or 60 instead of layer 68. If only one of electrodes 52 and 54 is placed on layer 68, layers 64 and 68 or layers 60 and 68 are placed sufficiently close such that the spacing between the closest edges or surfaces of electrodes 52 and 54 is maintained at less than 500 μm, preferably less than about 450, 400, 350, 300, or 250 μm, more preferably less than about 200, 150, or 100 μm, and most preferably less than about 90, 80, 70, 60, 50, 40, 30, 25, 20, 15, 10, 5 or 1 μm. In another embodiment, an additional layer (not illustrated) is placed on layer 68, and one or both of electrode 52 and electrode 54 may be placed on the additional layer.

Fabricating the Electrochemical Cell

The electrochemical cell of certain embodiments is disposable and designed for use in a single experiment. In preferred embodiments, the electrochemical cell may be fabricated using methods similar to those disclosed in U.S. Pat. No. 5,942,102. In one method of a preferred embodiment for preparing an electrochemical cell 10 as illustrated in FIG. 1, the layers of electrically resistive material 20, 22, 24, or 26 are polyester sheets having a sputter coating of palladium as the electrically conductive layer 12, 14, 16, or 18, the portion remaining exposed after fabrication forming the electrodes 32, 34, 36, or 38.

As will be recognized by one skilled in the art, the layers of electrically conductive material 12, 14, 16, 18 and layers of electrically resistive material 20, 22, 24, 26 may be independently selected as desired, for example, for ease of fabrication, for reducing materials costs, or to achieve other desirable attributes of the cell 10 or fabrication process. Likewise, the layers of electrically conductive material 12, 14, 16, 18 may be applied to the layers of electrically resistive material 20, 22, 24, 26 in any suitable pattern, for example, a pattern that only partially covers the electrically resistive layer 20, 22, 24, or 26.

Once the electrically conductive materials are coated on or otherwise adhered to the corresponding electrically resistive layers 20, 22, 24, or 26, the covered layers 40, 42 may then be adhered to each other to form an electrode bearing layer 48. In the electrochemical cell of FIG. 1, covered layer 40 is adhered to covered layer 42 with the conductive layer 16 adjacent to the electrically resistive layer 26 of covered layer 42. Covered layers 44 and 46 are likewise adhered to form an electrode-bearing layer 49.

In preferred embodiments, various layers in the cell may be adhered using a suitable adhesive. Suitable adhesives include, for example, heat activated adhesives, pressure sensitive adhesives, heat cured adhesives, chemically cured adhesives, hot melt adhesives, hot flow adhesives, and the like. Pressure sensitive adhesives are preferred for use in certain embodiments where simplification of fabrication is desired. However, in other embodiments the tackiness of pressure sensitive adhesives may result in fabrication tool gumming or product tackiness. In such embodiments, heat or chemically cured adhesives are generally preferred. Especially preferred are the heat-activated and heat-cured adhesives, which can be conveniently activated at the appropriate time.

In certain embodiments, it may be preferred to use a hot melt adhesive. A hot melt adhesive is a solvent-free thermoplastic material that is solid at room temperature and is applied in molten form to a surface to which it adheres when cooled to a temperature below its melting point. Hot melt adhesives are available in a variety of chemistries over a range of melting points. The hot melt adhesive can be in the form of a web, nonwoven material woven material, powder, solution, or any other suitable form. Polyester hot melt adhesives may be preferred for certain embodiments. Such adhesives (available, for example, from Bostik Corp. of Middleton, Mass.) are linear saturated polyester hot melts exhibiting melting points from 65° C. up to 220° C. and range from completely amorphous to highly crystalline in nature. Polyamide (nylon) hot melt adhesives, also available from Bostik, may also be preferred, including both dimer-acid and nylon-type polyamide adhesives. Suitable hot melt adhesive chemistries include EVA, polyethylene, and polypropylene.

Alternatively, in certain other embodiments it may be preferred to use lamination techniques to bond certain layers together. Suitable lamination techniques are described in copending application Ser. No. 09/694,120 filed Oct. 20, 2000 and entitled "Laminates of Asymmetric Membranes." The layers to be laminated are placed adjacent to each other and heat is applied, whereby a bond between the layers is formed. Pressure may also be applied to aid in forming the bond. Lamination methods may be preferred to bond any two materials capable of forming a bond under application of heat and/or pressure. Lamination is preferred to form a bond between two suitable polymeric materials.

The electrode bearing layers 48 and 49 are then fixed in position with the electrodes 32 and 34 facing electrodes 36 and 38. This is typically accomplished by adhering one or more shaped spacer layers (not illustrated) between the electrode bearing layers 48 and 49. The spacer layer is shaped so as to provide sample reservoirs 28 and 29 between the electrode bearing layers 48 and 49. The spacer layer may be in the form of a sheet of electrically resistive material with a portion of the sheet removed to form the sample reservoirs 28 and 29, for example, a circular portion centered in the middle of the sheet, or a portion removed along one edge of the sheet. The spacer layer may also include two or more shaped portions placed adjacent to each other with a space between, the space providing entry of sample into sample reservoirs 28 and 29 and the reservoirs themselves 28 and 29. Instead of a rigid or flexible sheet of material, a layer of electrically resistive adhesive may be preferred as the spacer. In such an embodiment, the adhesive is applied to the electrode side of an electrode bearing layer 48 or 49, then the other electrode bearing layer 49 or 48 is placed atop the adhesive layer and a bond is formed, for example, by pressure, curing, heat, or other suitable means.

In a preferred embodiment, the spacer layer is a sheet of electrically resistive material pierced by a circular aperture and adhered by an adhesive to the electrode bearing layers 48 and 49. The circular aperture is preferably centered along the edge of electrode 32 adjacent to electrode 38 (or the edge of electrode 34 adjacent to electrode 38). There is thereby defined a cell 10 having a cylindrical side wall closed on end by electrode bearing layer 48 and on the other side by electrode bearing layer 49. The assembly is notched to provide for sample to be admitted to the cell 10 or to be drawn in by wicking or capillary action and to allow air to escape. The electrode layers 32, 34, 36, 38 are connected with suitable electrical connections or formations whereby potentials may be applied and currents measured.

In another preferred embodiment, the spacer is formed by applying a pattern of adhesive to one or both of the electrode bearing layers 48, 49. This method may be preferred where ease of fabrication and reduction in material costs are desired.

Suitable electrically resistive materials which may be preferred as spacer layers, as supports for electrode layers, or in other layers in the cell, include, for example, materials such as polyesters, polystyrenes, polycarbonates, polyolefins, polyethylene terephthalate, glasses, ceramics, mixtures and/or combinations thereof, and the like. Examples of electrically resistive adhesives suitable for use as spacer layers include, but are not limited to, polyacrylates, polymethacrylates, polyurethanes, and sulfonated polyesters.

In embodiments wherein the spacer is a sheet of electrically resistive material with a portion removed to form the sample reservoirs 28 and 29, one electrode bearing layer 48 or 49 is mounted on one side of the sheet, extending over the aperture and forming an end wall. The electrode-bearing layer 48 or 49 may be adhered to the spacer sheet, for example, by an adhesive. Multiple spacer sheets may be adhered to each other so as to form a spacer that conforms to the stepped surfaces of the electrode bearing layers 48 and 49. A deformable adhesive may also be preferred as the spacer, the adhesive conforming to the contours of the electrode bearing layers 48 and 49. In a preferred embodiment, the overall shape of the combined sample reservoirs 28 and 29 is circular, however other shapes, for example, square, rectangular, polygonal, oval, ellipsoidal, irregular, or others, may be preferred for certain embodiments.

The second electrode bearing layer 49 or 48 is then mounted on the opposite side of the spacer, also extending over the aperture, so as to form a second end wall. Electrodes 32 and 34 are typically spaced less than about 500 µm apart, preferably less than about 450, 400, 350, 300, or 250 µm apart, more preferably less than about 200, 150, or 100 µm apart, and most preferably less than about 90, 80, 70, 60, 50, 40, 30, 25, 20, 15, 10, 5 or 1 µm. A second aperture or ingress is then provided for liquid to enter the cell 10. Such an ingress can be provided by forming a notch along one edge of the device, which extends through the electrode bearing layers 48 and 49 and aperture. The electrode bearing layers 48 and 49 are provided with connections allowing the electrodes to be placed in a measuring circuit.

As will be recognized by one skilled in the art, the techniques described above for fabricating an electrochemical cell as illustrated in FIG. 1 may be modified to fabricate an electrochemical cell as illustrated in FIG. 2.

Chemicals for use in the cell, such as redox reagents, lysing agents, buffers, inert salts, and other substances, may be supported on the cell electrodes or walls, on one or more independent supports contained within cell, or may be self supporting. If the chemicals are to be supported on the cell electrodes or walls, the chemicals may be applied by use of application techniques well known in the art, such as ink jet printing, screen printing, lithography, ultrasonic spraying, slot coating, gravure printing, and the like. Suitable independent supports may include, but are not limited to, meshes, nonwoven sheets, fibrous fillers, macroporous membranes, and sintered powders. The chemicals for use in the cell may be supported on or contained within a support.

In a preferred embodiment, the preferred materials within the cell as well as the materials from which the cell is constructed are in a form amenable to mass production, and the cells themselves are designed for a single experiment then disposed of. A disposable cell is one that is inexpensive enough to produce that it is economically acceptable only for a single test. A disposable cell is one that may conveniently only be used for a single test, namely, steps such as washing and/or reloading of reagents may need to be taken to process the cell after a single use to render it suitable for a subsequent use.

Economically acceptable in this context means that the perceived value of the result of the test to the user is the same or greater than the cost of the cell to purchase and use, the cell purchase price being set by the cost of supplying the cell to the user plus an appropriate mark up. For many applications, cells having relatively low materials costs and simple fabrication processes are preferred. For example, the electrode materials of the cells may be inexpensive, such as carbon, or may be present in sufficiently small amounts such that expensive materials may be preferred. Screen printing carbon or silver ink is a process suitable for forming electrodes with relatively inexpensive materials. However, if it is desired to use electrode materials such as platinum, palladium, gold, or iridium, methods with better material utilization, such as sputtering or evaporative vapor coating, are preferred as they may yield extremely thin films. The substrate materials for the disposable cells are also preferably inexpensive. Examples of such inexpensive materials are polymers such as polyvinylchloride, polyimide, polyester and coated papers and cardboard.

Cell assembly methods are preferably amenable to mass production. These methods include fabricating multiple cells on cards and separating the card into individual strips subsequent to the main assembly steps, and web fabrication where the cells are produced on a continuous web, which is subsequently separated into individual strips. Card processes are most suitable when close spatial registration of multiple features is desired for the fabrication and/or when stiff cell substrate materials are preferred. Web processes are most suitable when the down web registration of features is not as critical and flexible webs may be preferred.

A convenient single use for the disposable cell is desirable so that users are not tempted to try to reuse the cell and possibly obtain an inaccurate test result. Single use of the cell may be stated in user instructions accompanying the cell. More preferably, in certain embodiments where a single use is desirable the cell may be fabricated such that using the cell more than once is difficult or not possible. This may be accomplished, for example, by including reagents that are washed away or consumed during the first test and so are not functional in a second test. Alternatively, the signal of the test may be examined for indications that reagents in the cell have already reacted, such as an abnormally high initial signal, and the test aborted. Another method includes providing a means for breaking electrical connections in the cell after the first test in a cell has been completed.

The Electrodes

In a preferred embodiment wherein the electrochemical cell detects the presence and/or amount of analyte in the sample, or a substance indicative of the presence and/or amount of analyte present in the sample, at least one of the electrodes in the cell is a working electrode. When the potential of the working electrode is indicative of the level of analyte (such as in a potentiometric sensor) a second electrode acting as reference electrode is present which acts to provide a reference potential.

In the case of an amperometric sensor wherein the working electrode current is indicative of the level of an analyte, such as glucose, at least one other electrode is preferably present which functions as a counter electrode to complete the electrical circuit. This second electrode may also function as a reference electrode. Alternatively, a separate electrode may perform the function of a reference electrode.

Materials suitable for the working, counter, and reference electrodes are compatible with any reagents or substances present in the device. Compatible materials do not substantially react chemically with other substances present in the cell. Examples of such suitable materials may include, but are not limited to, carbon, carbon and an organic binder, platinum, palladium, carbon, indium oxide, tin oxide, mixed indium/tin oxides, gold, silver, iridium, and mixtures thereof. These materials may be formed into electrode structures by any suitable method, for example, by sputtering, vapor coating, screen printing, thermal evaporation, gravure printing, slot coating or lithography. In preferred embodiments, the material is sputtered or screen-printed to form the electrode structures.

Non-limiting examples of materials preferred for use in reference electrodes include metal/metal salt systems such as silver in contact with silver chloride, silver bromide or silver iodide, and mercury in contact mercurous chloride or mercurous sulfate. The metal may be deposited by any suitable method and then brought into contact with the appropriate metal salt. Suitable methods include, for example, electrolysis in a suitable salt solution or chemical oxidation. Such metal/metal salt systems provide better potential control in potentiometric measurement methods than do single metal component systems. In a preferred embodiment, the metal/metal salt electrode systems are preferred as a separate reference electrode in an amperometric sensor.

The Lysing Agent

In certain embodiments, it may be desired to include one or more lysing agents in the electrochemical cell. Suitable lysing agents include detergents, both ionic and non-ionic, proteolytic enzymes, and lipases. Suitable ionic detergents include, for example, sodium dodecyl sulfate and cetyl trimethylammonium bromide. Non-limiting examples of proteolytic enzymes include trypsin, chymotrypsin, pepsin, papain, and Pronase E, a very active enzyme having broad specificity. Nonionic surfactants suitable for use include, for example, ethoxylated octylphenols, including the Triton X Series available from Rohm & Haas of Philadelphia, Pa. In a preferred embodiment, saponins, namely, plant glycosides that foam in water, are preferred as the lysing agent.

The Redox Reagent

Redox reagents may also be included in the electrochemical cell in preferred embodiments. Preferred redox reagents for use in electrochemical cells for measuring glucose in blood include those which are capable of oxidizing the reduced form of enzymes that are capable of selectively oxidizing glucose. Examples of suitable enzymes include, but are not limited to, glucose oxidase dehydrogenase, PQQ dependent glucose dehydrogenase, and NAD dependent glucose dehydrogenase. Examples of redox reagents suitable for use in analyzing glucose include, but are not limited to, salts of ferricyanide, dichromate, vanadium oxides, permanganate, and electroactive organometallic complexes. Organic redox reagents such as dichlorophenolindophenol, and quinones are also suitable. In a preferred embodiment, the redox reagent for analyzing glucose is ferricyanide.

The Buffer

Optionally, a buffer may be present along with a redox reagent in dried form in the electrochemical cell. If a buffer is present, it is present in an amount such that the resulting pH level is suitable for adjusting the oxidizing potential of the redox reagent to a level suitable for oxidizing, for example, glucose but not other species that it is not desired to detect. The buffer is present in a sufficient amount so as to substantially maintain the pH of the sample at the desired level during the test. Examples of suitable buffers include phosphates, carbonates, alkali metal salts of mellitic acid, and alkali metal salts of citric acid. The choice of buffer may depend, amongst other factors, on the desired pH. The buffer is selected so as not to react with the redox reagent.

Inert Salts

Inert salts preferred for use in various embodiments include salts that dissociate to form ions in the sample to be analyzed, but do not react with any of the redox reagents or other substances in the sample or in the cell, including with the cell electrodes. Examples of suitable inert salts include, but are not limited to, alkali metal chlorides, nitrates, sulfates, and phosphates.

Other Substances Present within the Cell

In addition to redox reagents and buffers, other substances may also be present within the electrochemical cell. Such substances include, for example, viscosity enhancers and low molecular weight polymers. Hydrophilic substances may also be contained within the cell, such as polyethylene glycol, polyacrylic acid, dextran, and surfactants such as those marketed by Rohm & Haas Company of Philadelphia, Pa., under the trade name Triton™, or by ICI Americas Inc. of Wilmington, Del., under the trade name Tween™. Such substances may enhance the fill rate of the cell, provide a more stable measurement, and inhibit evaporation in small volume samples.

Electrical Circuit

The electrically conductive layers are preferably connected to electrical circuits capable of applying potentials between the electrodes and measuring the resulting currents, for example, meters. Any suitable means for connecting an electrically conductive layer to an electrical circuit may be preferred, including, but not limited to, a tongue plug, a set of connection pins that are brought down on top of the strip or up from below the strip, and the like. The connection areas are not illustrated in FIG. 1. Suitable meters may include one or more of a power source, circuitry for applying controlled potentials or currents, a microprocessor control device, computer, or data storage device, a display device, an audible alarm device, or other devices or components as are known in the art. The meter may also be capable of being interfaced to a computer or data storage device. For example, a typical meter may be a hand-held device that is powered by a battery, controlled by an on-board microprocessor, and contains circuitry for applying predetermined potentials or currents between, for example, strip electrode connection pins and circuitry such as an analog-to-digital converter. In this embodiment, the analog signal from the strip may be converted to a digital signal that can be analyzed and/or stored by a microprocessor. The meter may also contain a display such as a Liquid Crystal Display and suitable associated circuitry to display the result of the test to the user. In an alternative embodiment, the meter may incorporate specialized circuitry, such as potential application and signal acquisition circuitry. Such specialized circuitry may be incorporated in a separate module that may be interfaced with a generic computing device, such as a hand-held computer or other type of computer. In such an embodiment, the generic device may perform the control, analysis, data storage, and/or display functions. Such an embodiment allows for a less expensive meter to be produced because the generic computing device may be preferred for many functions and as such is not considered as part of the cost of the electrochemical measurement system. In either of these meter embodiments, the meter or generic computing device may be capable of communication with external devices such as local computer networks or the Internet to facilitate the distribution of test results and the provision of system upgrades to the user.

Obtaining Electrochemical Measurements

An electrochemical cell as shown in FIG. 1 or FIG. 2 may be used to provide improved analyte detection. However, for purposes of illustration, the methods of preferred embodiments are discussed in regard to the electrochemical cell 10 of FIG. 1 wherein electrode 34 and electrode 38 are set as working electrodes and electrode 36 and electrode 32 as counter electrodes. The analyte in this context can be the actual specie(s) of interest in the sample or can be products of chemical reactions with the specie(s) of interest. Electrodes 32 and 34 are spaced closely enough such that the products of electrochemical reactions at electrode 32 diffuse to and react at electrode 34 during the time of the test. This spacing is typically less than about 500 µm, preferably less than about 450, 400, 350, 300, or 250 µm, more preferably less than about 200, 150, or 100 µm, and most preferably less than about 90, 80, 70, 60, 50, 40, 30, 25, 20, 15, 10, 5 or 1 µm. Electrodes 36 and 38, however, are spaced far enough apart such that the products of reaction at electrode 36 do not reach electrode 38 during the test. This space is typically greater than about 500 µm, preferably greater than about 550, 600, 650, 700, 750, 800, 850, 900, or 950 µm and most preferably greater than about 1, 2, 3, 4, 5, 6, 7, 8, 9, 10, 25, or 50 mm. In any case, the gap between electrode 36 and electrode 38 is typically substantially larger than the gap between electrode 32 and electrode 34.

When solution containing the analyte fills the spaces 29 and 28, a potential is applied between electrode 32 and electrode 34 by a first external circuit and between electrode 36 and electrode 38 by a second external circuit. These potentials are of a polarity such that the analyte is electrochemically reacted at electrode 34 and electrode 38 and of sufficient size such that the rate of electrochemical reaction is limited by the rate of mass transport of analyte to electrode 34 or electrode 38. As the potentials continue to be applied products of the electrochemical reactions at electrode 32 diffuse to electrode 34 and are reacted, however, there is no time for any significant amount of the products of the reactions at electrode 36 to reach electrode 38. By subtracting the current flowing between electrode 36 and electrode 38 from that flowing between electrode 32 and electrode 34, a current versus time signal can be obtained which is due only to the reaction at electrode 34 of the products of the electrochemical reactions at electrode 32. In order to obtain this current accurately, electrode 34 and electrode 38 either have to be of the same area, or the separate currents normalized by their respective working electrode areas prior to the current subtraction.

The advantage of obtaining the current only due to the reaction of counter electrode products at the working electrode is that contributions from other extraneous currents are eliminated. These extraneous currents include currents due to reaction of electrode surface groups, currents due to the oxidation or reduction of adsorbed species, and the electrode charging current, that is, the current that flows to polarize the electrode/solution double layer to the potential that is being applied across the interface by the external circuit. These currents flow at short times and limit the shortness of time at which current related to the analyte can be obtained with any certainty. By using this method to eliminate the extraneous current contributions, the current signal at shorter times can be used to obtain information about the analyte with increased certainty. It is desirable to be able to use the current signal at shorter times as it allows electrode 32 and electrode 34 to be placed closer together than may otherwise be practical. By placing electrode 32 and electrode 34 closer, the products from the reaction at electrode 32 reach electrode 34 faster and in higher amount. This increases the current signal and shortens the time period over which the currents are monitored to obtain the desired analyte information.

In this method of a preferred embodiment, electrodes 32 and 34 form one circuit with a power supply to apply a suitable potential between electrodes 32 and 34. A second circuit, separate from the first, is formed between electrodes 36 and 38 and a power supply such that the current flowing between electrodes 32 and 34 and the current flowing between electrodes 36 and 38 can be measured separately. Alternatively, rather than measuring the currents separately, the two currents can be subtracted electronically and the resulting subtracted current measured.

In a second method of a preferred embodiment, an electrode arrangement can be used to effectively amplify the current signal arising from reaction of the analyte. In this method, electrode 32 is used as a counter electrode for both electrode 34 and electrode 38 during at least a portion of the test. A reagent is dried or otherwise deposited within the space between electrode 32 and 34, the reagent including a mediator that is electrochemically reversible and preferably also reacts chemically with the analyte of interest to produce a reacted mediator, wherein the reacted mediator is capable of reacting electrochemically at electrode 34 and being electrochemically generated at electrode 32 from mediator. The reagent deposited within space 28 may contain a mediator or, when the analyte is capable of reacting directly at the electrode 38, may not contain a mediator.

During a test, potentials are applied such that the analyte and/or the mediator that has chemically reacted with the analyte electrochemically react at electrode 34 and 38. The counter electrode used to complete the circuit for both electrode 34 and electrode 38 in this method of use is electrode 32. Electrons gathered from reactions with the analyte or reacted mediator at electrode 38 leads to an equal amount of reacted mediator being produced at 32. This reacted mediator can then travel to electrode 34 and react to be returned to mediator. In this way the current arising from the analyte or reacted mediator in the volume of solution in space 28 is used to produce a corresponding amount of reacted mediator in the volume of solution in space 29, thus effectively concentrating a specie related to the analyte from space 28 into space 29 producing an enhanced current signal from the analyte. Due to the diffusion distances involved, the reacted mediator in space 29 remains substantially in space 29 during the test. To ensure that this is the case, it is preferred to have the length of space 29 longer than the distance between electrode 36 and electrode 38. In this case, in the time it takes for mediator to diffuse from electrode 36 to electrode 38, only a small fraction of the material in space 29 diffuses into space 28.

By way of an example of this method, if the area of electrode 38 is ten times that of electrode 34 and the thickness of space 28 is ten times the thickness of space 29, then the concentration of the reacted mediator in space 29 is up to 101 times that present than if just electrode 32 and electrode 34 are used. In this example, therefore, the detection limit of the analyte is lowered by up to 101 times. For example, if the concentration of analyte or reacted mediator in the solution filling spaces 29 and 28 was originally X, then after substantially all of the analyte or reacted mediator in the solution above electrode 38 has been electrochemically reacted at electrode 38, that number of moles of analyte or reacted mediator has produced a corresponding number of moles of reacted mediator in the space 29. Since in this example the volume of solution above electrode 38 is 100 times the volume of the space 29 the concentration of reacted mediator in space 29 is now X+100·X, the original amount in the space 29 plus 100 times the original amount due the reactions at electrode 38. Note that it is not necessary to react all the analyte or reacted mediator in the solution above electrode 38 for this method to have utility. In some cases, for instance where it is desirable to sacrifice some signal amplification for a shorter test time, only a fraction of the analyte or reacted mediator in the solution above electrode 38 is reacted, as long as the fraction of species reacted is useful in that it is sufficient to obtain a useful signal amplification.

Optionally, in order to further reduce electrical noise, after the desired fraction (typically substantially all) of the analyte or reacted mediator have been electrochemically reacted at electrode 38, the circuit between electrode 32 and electrode 38 can be disconnected, leaving just electrode 32 and electrode 34 with a potential between them. The current flowing between electrode 32 and electrode 34 can then be monitored to determine the concentration of reacted mediator in space 29, which is related in a known way to the original analyte concentration. This procedure reduces electrical noise during the concentration determination as noise generated from electrode 38 is eliminated. The time at which the circuit between electrode 32 and electrode 38 is disconnected can, for example, be determined by setting a threshold current between electrode 32 and electrode 38 below which the disconnection occurs. Note that in this method of measuring current, the second counter electrode 36 is not necessary and so can be omitted.

A further optional method for reducing electrical noise due to electrode charging and other extraneous currents is to use electrode 36 as the counter electrode for electrode 38 during the electrode charging phase immediately after the potential has been applied between electrode 36 and electrode 38. After electrode 38 is polarized to the correct potential, the counter electrode for electrode 38 can be switched to be electrode 32. The time at which the counter electrode is switched can, for example, be set at a fixed time at which it is known that the electrode charging and surface group reactions are substantially over but before a substantial amount of the analyte or reacted mediator has reacted at electrode 38. If electrode 36 and electrode 38 are of substantially equivalent area then the charging current does not lead to any substantial amount of additional reacted mediator being formed due to the charging process.

A further optional method for reducing noise due to electrode charging and other extraneous currents is to use electrode 36 as the counter electrode for electrodes 34 and 38 during the electrode charging phase immediately after the potential has been applied to electrodes 34 and 38. After electrodes 34 and 38 are polarized to the correct potential and after the electrochemical reaction of some or all of the surface and adsorbed groups or reacted mediator present in any dried reagent layers adjacent to electrode 34, the counter electrode for electrodes 34 and 38 can be switched to electrode 36. As above, the time of the switching the counter electrode can be at a fixed time. This procedure allows for the effect of extraneous reacted mediator or other electrochemically reactive species to be lessened or eliminated. In these two options, the second counter electrode 36 is present.

In the above-mentioned methods, it is desirable that an electrochemically inert soluble salt, at a concentration substantially higher than the analyte, also be present in the solution filling the cell, either derived from the sample itself or from reagents deposited into the cell. This inert salt serves to carry electrical current in the solution between space 29 and space 28 when electrode 32 is used as the counter electrode for electrode 38, minimizing the loss of reacted mediator from space 29 due to electromigration.

The above description provides several methods and materials of the present invention. This invention is susceptible to modifications in the methods and materials, as well as alterations in the fabrication methods and equipment. Such modifications will become apparent to those skilled in the art from a consideration of this disclosure or practice of the invention provided herein. Consequently, it is not intended that this invention be limited to the specific embodiments provided herein, but that it cover all modifications and alternatives coming within the true scope and spirit of the invention as embodied in the attached claims.

What is claimed is:

1. A method for determining a concentration of a reduced or oxidized form of a redox species, the method comprising the steps of:
    a) providing an electrochemical cell comprising a first working electrode, a first counter electrode, a second working electrode and a second counter electrode;
    b) selecting a spacing between the first working electrode and the first counter electrode such that reaction products from the first counter electrode arrive at the first working electrode;
    c) selecting a spacing between the first working electrode and the second counter electrode such that a significant amount of reaction products from the second counter electrode do not arrive at the first working electrode;
    d) selecting a spacing between the second working electrode and the second counter electrode such that a significant amount of reaction products from the second counter electrode do not arrive at the second working electrode;
    e) applying an electric potential difference between the first working electrode and the first counter electrode;
    f) applying an electric potential difference between the second working electrode and second counter electrode;
    g) selecting a potential of the first working electrode such that a rate of electro-oxidation of a reduced form of a redox species or a rate of electro-reduction of an oxidized form of a redox species is diffusion controlled;
    h) selecting a potential of the second working electrode such that a rate of electro-oxidation of the reduced form of a redox species or a rate of electro-reduction of an oxidized form of a redox species is diffusion controlled;

i) subtracting a current flowing between the second working electrode and the second counter electrode from a current flowing between the first working electrode and the first counter electrode, whereby a corrected current is obtained; and j) obtaining from the corrected current a value indicative of the concentration of the reduced form of the redox species or the oxidized form of the redox species.

2. The method according to claim 1, wherein a surface area of the first working electrode and a surface area of the second working electrode are substantially the same.

3. The method according to claim 1, wherein a surface area of the first working electrode and a surface area of the second working electrode are different, wherein step i) comprises:

determining a current flowing between the first working electrode and the first counter electrode;

determining a current flowing between the second working electrode and the second counter electrode;

normalizing the current flowing between the first working electrode and the first counter electrode and the current flowing between the second working electrode and the second counter electrode to a same electrode surface area to yield a normalized current flowing between the first working electrode and the first counter electrode and a normalized current flowing between the second working electrode and the second counter electrode; and subtracting the normalized current flowing between the second working electrode and the second counter electrode from the normalized current flowing between the first working electrode and the first counter electrode, whereby a corrected current is obtained.

4. The method according to claim 1 wherein the first working electrode and the first counter electrode are separated by less than about 500 μm.

5. The method according to claim 1 wherein the first working electrode and the first counter electrode are separated by less than about 200 μm.

6. The method according to claim 1 wherein the second working electrode and the second counter electrode are separated by more than about 500 μm.

7. The method according to claim 1 wherein the first working electrode and the second counter electrode are separated by more than about 500 μm.

8. The method according to claim 1 wherein the second working electrode and the second counter electrode are separated by more than about 1 mm.

9. The method according to claim 1 wherein the first working electrode and the second counter electrode are separated by more than about 1 mm.

10. The method according to claim 1 wherein the redox species is a mediator and the concentration of the reduced or oxidized form of the mediator is indicative of a concentration of an analyte and wherein a measure of a diffusion coefficient of a reduced or oxidized form of the mediator is determined as a precursor to the determination of the concentration of the analyte.

11. The method according to claim 10 wherein the analyte is glucose.

12. The method according to claim 1 wherein the redox species is a mediator.

13. The method according to claim 1 wherein the electrochemical cell additionally comprises a separate reference electrode.

14. Apparatus for determining the concentration of a redox species in an electrochemical cell comprising: an electrochemical cell having a first working electrode, a first counter electrode, a second working electrode and a second counter electrode, characterized in that the first working electrode is spaced from the first counter electrode by less than 500 μm, the first working electrode is spaced from the second counter electrode by more than 500 μm, and the second working electrode is spaced from the second counter electrode by more than 500 μm; an electrical circuit capable of applying an electric potential difference between the first working electrode and the first counter electrode; and an electrical circuit capable of applying an electric potential difference between the second working electrode and the second counter electrode.

15. The apparatus according to claim 14, wherein the apparatus is a glucose meter.

16. A method for determining a concentration of a reduced or oxidized form of a redox species, the method comprising the steps of:

a) providing an electrochemical cell comprising a first working electrode, a second working electrode, and a counter electrode;

b) selecting a spacing between the first working electrode and the counter electrode such that reaction products from the counter electrode arrive at the first working electrode;

c) selecting a spacing between the second working electrode and the counter electrode such that a significant amount of reaction products from the counter electrode do not arrive at the second working electrode;

d) applying an electric potential difference between the second working electrode and the counter electrode whereby the second working electrode is substantially charged and whereby surface group reactions are substantially completed;

e) interrupting a circuit between the second working electrode and the counter electrode before a significant amount of the redox species is reacted at the second working electrode;

f) applying an electric potential difference between the first working electrode and the counter electrode;

g) selecting a potential of the first working electrode such that a rate of electro-oxidation of the reduced form of the redox species or a rate of electro-reduction of the oxidized form of the redox species is diffusion controlled;

h) determining a current flowing between the first working electrode and the counter electrode; and i) obtaining from the current a value indicative of a concentration of the reduced form of the redox species or the oxidized form of the redox species.

17. A method for determining a concentration of a reduced or oxidized form of a redox species, the method comprising the steps of:

a) providing an electrochemical cell comprising a first working electrode, a second working electrode, and a counter electrode;

b) selecting a spacing between the first working electrode and the counter electrode such that reaction products from the counter electrode arrive at the first working electrode;

c) selecting a spacing between the second working electrode and the counter electrode such that a significant amount of reaction products from the counter electrode do not arrive at the second working electrode;

d) applying an electric potential difference between the second working electrode and the counter electrode and between the first working electrode and the counter electrode, whereby the second working electrode and first working electrode are substantially charged and whereby surface group reactions are substantially completed;

e) interrupting a circuit between the second working electrode and the counter electrode before a significant amount of the species is reacted at the second working electrode;

f) applying an electric potential difference between the first working electrode and the counter electrode;

g) selecting a potential of the first working electrode such that a rate of electro-oxidation of the reduced form of the redox species or a rate of electro-reduction of the oxidized form of the redox species is diffusion controlled;

h) determining a current flowing between the first working electrode and the counter electrode; and i) obtaining from the current a value indicative of a concentration of the reduced form of the redox species or the oxidized form of the redox species.

18. Apparatus for determining a concentration of a redox species in an electrochemical cell comprising: an electrochemical cell having a first working electrode, a first counter electrode, a second working electrode and a second counter electrode, characterized in that the first working electrode is spaced from the first counter electrode by less than 500 µm, the first working electrode is spaced from the second counter electrode by more than 500 µm, and the second working electrode is spaced from the second counter electrode by more than 500 µm; means for applying an electric potential difference between the first working electrode and the first counter electrode; and means for applying an electric potential difference between the second working electrode and the second counter electrode.

19. The apparatus according to claim 18, wherein the apparatus is a glucose meter.

20. An electrochemical cell comprising a first working electrode, a first counter electrode, a second working electrode, and a second counter electrode, the first working electrode being spaced from the first counter electrode by less than about 500 µm, the first working electrode being spaced from the second counter electrode by more than about 500 µm, and the second working electrode facing the second counter electrode and being spaced from the second counter electrode by more than about 500 µm.

21. The electrochemical cell according to claim 20, wherein the first working electrode and the first counter electrode are facing one another.

22. The electrochemical cell according to claim 20, wherein the first working electrode and the first counter electrode are in a side-by-side configuration.

23. The electrochemical cell according to claim 20, wherein the first working electrode and the second working electrode are of substantially corresponding area.

24. The electrochemical cell according to claim 20, further comprising a separate reference electrode.

25. The electrochemical cell of claim 20, wherein the electrochemical cell is a hollow electrochemical cell.

26. The electrochemical cell according to claim 25, having an effective cell volume of less than 1.5 microliters.

* * * * *